(12) United States Patent
Janssen et al.

(10) Patent No.: US 8,696,609 B2
(45) Date of Patent: Apr. 15, 2014

(54) MULTI-FUNCTION SWITCH FOR AN ORAL CARE APPLIANCE

(75) Inventors: Jozef Johannes Maria Janssen, Herten (NL); Bart Gottenbos, Budel (NL); Petrus Henricus De Leeuw, Someren (NL)

(73) Assignee: Koninklijke Philips N.V., Eindhoven (NL)

( * ) Notice: Subject to any disclaimer, the term of this patent is extended or adjusted under 35 U.S.C. 154(b) by 869 days.

(21) Appl. No.: 12/808,248

(22) PCT Filed: Dec. 9, 2008

(86) PCT No.: PCT/IB2008/055169
§ 371 (c)(1),
(2), (4) Date: Jun. 15, 2010

(87) PCT Pub. No.: WO2009/077923
PCT Pub. Date: Jun. 25, 2009

(65) Prior Publication Data
US 2010/0273125 A1     Oct. 28, 2010

Related U.S. Application Data

(60) Provisional application No. 61/014,489, filed on Dec. 18, 2007.

(51) Int. Cl.
*A61C 17/02* (2006.01)
(52) U.S. Cl.
USPC ............... 601/161; 601/162; 433/80; 433/89
(58) Field of Classification Search
USPC ......... 601/154, 155, 160, 161, 162, 165, 169; 433/80, 82, 89, 114, 120; 604/131, 604/141, 249; 239/154
See application file for complete search history.

(56) References Cited

U.S. PATENT DOCUMENTS

| 4,149,315 A | 4/1979 | Page, Jr. et al. |
| 4,583,531 A * | 4/1986 | Mattchen ................ 601/161 |
| 5,046,486 A * | 9/1991 | Grulke et al. ........... 601/161 |
| 6,824,385 B1 * | 11/2004 | Bain et al. ................ 433/80 |
| 2002/0082545 A1 | 6/2002 | Sennett et al. |

FOREIGN PATENT DOCUMENTS

| WO | 9817198 | 4/1998 |
| WO | 2005076818 A2 | 8/2005 |
| WO | 2008012707 A2 | 1/2008 |

* cited by examiner

*Primary Examiner* — Quang D Thanh

(57) ABSTRACT

A multi-switch (24) for an oral care appliance includes a switch housing (28) having a hollow chamber (30) therein, a button actuator (32) with at least two O-rings (42) around the periphery thereof, and inlet and outlet channels (50, 52) connecting a source of compressed gas (18) with the housing chamber and the housing chamber with a mixing chamber (26), respectively. A pump (60) moves fluid from a reservoir (20) to the mixing chamber. The O-rings are positioned so that as the button actuator is actuated and then released, the outlet is closed and the inlet is opened, allowing gas to move into the housing chamber. The pump is actuated, and then the inlet is closed and the outlet opens, allowing gas in the chamber to move to the mixing chamber to produce a stream of fluid droplets, which are directed out through a nozzle portion (16) of the appliance.

14 Claims, 2 Drawing Sheets

MULTI-FUNCTION SWITCH FOR AN ORAL CARE APPLIANCE

TECHNICAL FIELD

This invention relates generally to an oral care appliance which uses pressurized gas and liquid to accomplish teeth cleaning, and more specifically concerns a switch assembly which actuates multiple functions of the appliance.

BACKGROUND OF THE INVENTION

In many oral care appliances, including specifically power appliances using pressurized gas and liquid, several individual, separate functions must be controlled and sequenced for proper operation of the appliance. Typically, this requires the use of a plurality of individual switches and/or other actuators in a particular sequence. Significant operational capability is achieved with such a system, but at additional expense and complexity. It would thus be desirable to have a single switch assembly which can control a plurality of individual functions in a correct sequence so as to reduce cost as well as improving the reliability.

SUMMARY OF THE INVENTION

Accordingly, a multi-function switch for an oral care appliance is disclosed which includes a source of compressed gas, a source of liquid and a mixing chamber for mixing the gas and the fluid to produce a stream of fluid droplets directed out through a nozzle assembly, comprising: a switch housing having a hollow chamber therein; an actuation assembly which includes a stem portion having an O-ring assembly around the periphery thereof; an inlet channel connecting the source of compressed gas to the hollow chamber in the housing; an outlet channel connecting the hollow chamber to the mixing chamber; wherein the O-rings are positioned on the stem relative to the inlet channel and the outlet channel such that in a first position of the actuation assembly, one O-ring seals the inlet channel at the chamber and, as the actuation assembly is actuated, the stem moves such that the outlet channel at the chamber is or continues to be sealed by another O-ring, and the inlet channel is uncovered, allowing into the chamber an amount of gas, while at that point or thereafter a pump is activated to move liquid into the mixing chamber; wherein when the actuation assembly is thereafter released to return to its first position, the inlet channel is first sealed and the outlet channel is subsequently uncovered, allowing the gas in the chamber to rapidly move into the mixing chamber to mix with the liquid therein, to produce a stream of fluid droplets which are directed to and out a nozzle portion of the appliance.

DETAILED DESCRIPTION OF THE INVENTION

Figure 1:
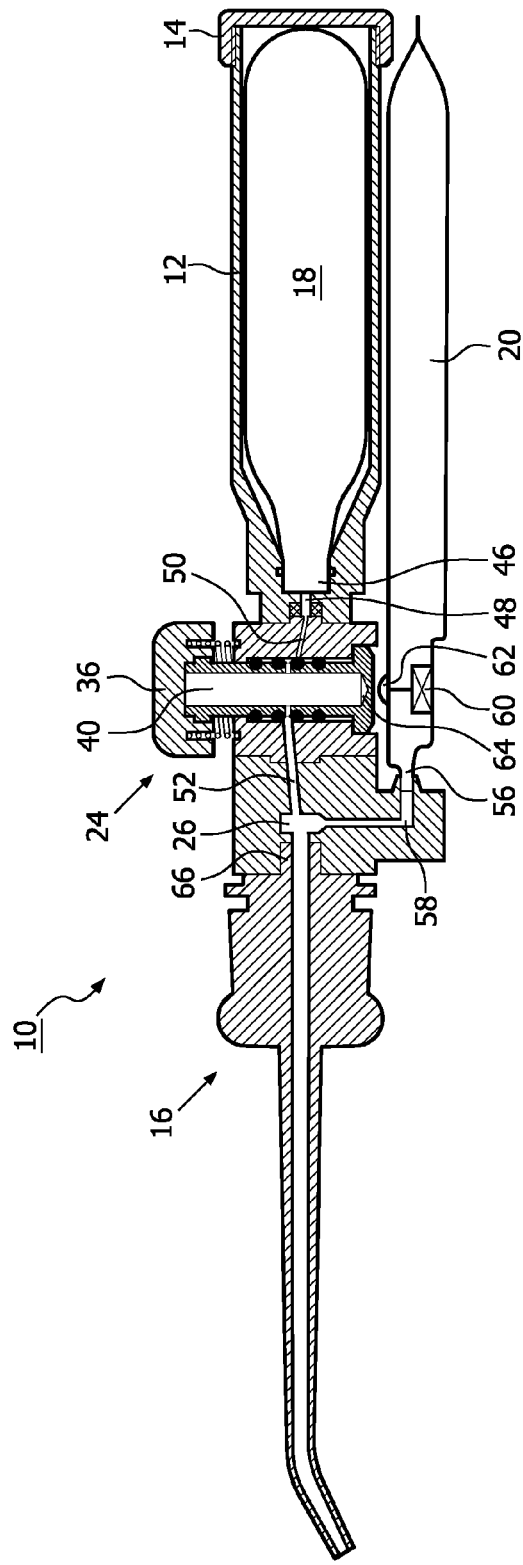
FIG. 1 is a longitudinal cross-sectional view of an oral care appliance incorporating a multi-function switch disclosed herein.

FIG. 1 shows an oral care appliance which is particularly adapted for cleaning interproximal areas of the teeth, but which can also clean the exposed surfaces of the teeth as well. The appliance, shown generally at 10, includes a housing 12, with an end or base cap/plug 14 at a rear end and a nozzle assembly 16 extending from the other end. The appliance 10 in general operation uses a source of compressed gas, such as a $CO_2$ cartridge 18, and a source of liquid, stored in a reservoir 20, to produce a stream of fluid droplets directed through nozzle 16 for use in oral cleaning, including cleaning the interproximal areas of the teeth. Such an appliance is in general well-known.

In the embodiment shown, a multi-function switch 24, which function in some respects like a valve, is used to control a metered, i.e. fixed, amount of pressurized gas from cartridge 18 and liquid from reservoir 20 into a mixing chamber 26, where the liquid is mixed with the pressurized gas to produce the stream of liquid droplets, which are then directed through nozzle assembly 16 to the teeth.

Switch assembly 24 includes a housing 28 having a hollow interior chamber 30 therein. Housing 28 is configured to extend laterally across the longitudinal dimension of the appliance, but other arrangements and configurations for the switch 24 are possible.

Figure 2:
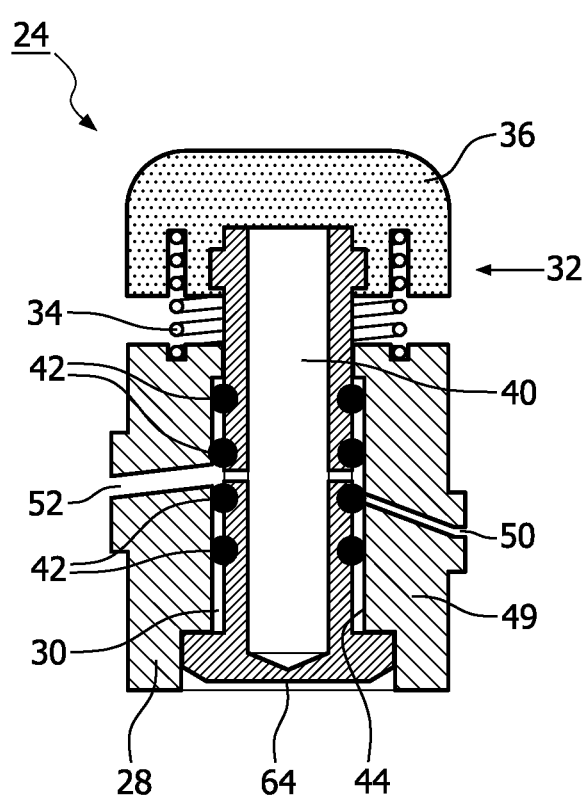
FIG. 2 is a cross-sectional view of the multi-function switch portion of the appliance of FIG. 1.

Mounted in housing 28 is a button assembly 32 which is biased by a spring 34 in a first position. Button assembly 32 includes a button 36 which is generally round and otherwise configured to conveniently accommodate a finger of the user. In the first position of the button assembly, button 36 is positioned slightly away from the housing. Button assembly 32 also includes a stem 40 which fits into chamber 30 of housing 28 in an air-tight relationship. Operation, i.e. pushing, of button 36 in a direction toward housing 28, moves stem portion 40 within housing 28. Mounted in the peripheral surface of stem are several O-rings 42-42 (FIG. 2) at spaced intervals along the stem. In the embodiment shown, there are four separate O-rings 42-42. The O-rings 42 extend from the surface of stem 40 to the interior wall 44 of chamber 30.

Extending from a forward end 46 of the $CO_2$ cartridge 18 is a hollow needle 48. Hollow needle 48 mates with an inlet channel 50 which extends through the wall 49 of housing 28 of the switch assembly to chamber 30. In the embodiment shown, channel 50 is positioned at an angle through wall 49 of housing 28. When button assembly 32 is in its first (non-operated or rest) position, one of the O-rings 42 covers, i.e. seals, the opening of inlet channel 50 into chamber 30, preventing any gas from the $CO_2$ cartridge from entering the chamber.

Extending through the wall 49 of housing 28 on the opposite side of chamber 30 is an outlet channel 52. Outlet channel 52 is also angled and opens into chamber 30 at a different longitudinal point than inlet channel 50 along the length of chamber 30. In the embodiment shown, the inlet and outlet channels are circular in cross-section, approximately 2 millimeters in diameter, although this may be varied. When button assembly 32 is in its first (non-operated) position, the opening of outlet channel 52 from chamber 30 is open, although in another arrangement, an O-ring 42 closes off the outlet channel 52 in the first position of the button assembly.

The forward end 56 of liquid reservoir 20 is connected through a fluid channel 58 to mixing chamber 26. Reservoir 20 includes a manual pump 60, by which liquid from the reservoir is moved through channel 58 into mixing chamber 26. Pump 60 is positioned so that an actuating portion 62 thereof extends into chamber 30 a small distance for contact with a distal end 64 of stem 40 when button assembly 32 is operated.

In operation, when button assembly 32 is in its first (non-operated/rest) position, inlet channel 50 at the entrance to chamber 30 is closed off by one O-ring 42. the O-rings 42 are mounted on stem 40 such that when button 36 is pushed, moving to its second, operated position, another of the O-rings 42 first seals the exit to outlet channel 52. This is accomplished while the inlet channel 50 into chamber 30 is sealed. Alternatively, outlet channel could have already been sealed and remains sealed while button 36 is pushed. Subsequent to outlet channel 52 being sealed, inlet channel 50 is opened, by virtue of the O-ring at that channel moving away from that channel opening as stem 40 moves within the chamber due to the pushing of the button 36. At this point, a specific, metered volume of gas enters into the chamber 30 through angled inlet channel 50. The defined volume of the chamber results in a precise amount of gas entering the chamber before the pressure is equalized between the chamber 30 and the cartridge.

The operation of button assembly 32 also results in distal end 64 of stem 40 actuating pump 60, resulting in a selected amount of liquid being moved from reservoir 20 directed through channel 58 into mixing chamber 26.

The button 36 is then released, which allows spring 34 to return the button assembly 32 to its first position, which results first in one O-ring 42 sealing the inlet channel 50 again and then, subsequent thereto, one O-ring 42 which previously sealed outlet channel 52 moving away from the outlet channel, resulting in the angled outlet channel being opened. In an alternative arrangement, an outlet slot in the outlet of the chamber is provided to receive the O-ring. In this arrangement, the O-ring is forced by the high pressure gas present in the chamber into the slot, opening the path for the gas to flow into the outlet instantaneously, such that the opening of the outlet is independent of the action of the user after gas has entered the chamber. This results in the gas present in chamber 30 expanding out through channel 52 into mixing chamber 26, where the mixing of the pressurized gas from the chamber 30 and the liquid from reservoir 20 results in a stream of liquid droplets which proceed from the mixing chamber 26 into the proximal end 66 of nozzle assembly 16. The liquid droplets continue through the nozzle assembly 16 to the outlet therefrom, for use in cleaning of teeth. The nozzle assembly 16 could also include a guidance tip which is designed to fit in the interproximal areas of the teeth.

In addition to the above, switch 10 could be configured to accomplish other functions as it is moved from its first (rest) to its second (operative) position and vice versa. For instance, electrical contacts could be positioned within chamber 30 volume so that movement of the button assembly could connect the contacts to operate another switch or activate a circuit to accomplish other functions, such as energizing an LED or status indicator or other similar function.

Hence, a switch assembly has been disclosed which, in operation, will produce a sequence of specific operations of the appliance. A single switch structure can thus accomplish a plurality of different functions, in a desired sequence.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. An oral care appliance comprising:
a source of compressed gas, a source of liquid, a mixing chamber for mixing the gas and the liquid to produce a stream of fluid droplets directed out through a nozzle assembly;
a switch housing having a hollow chamber therein;
an actuation assembly which is actuatable and releasable and includes a stem having an O-ring assembly comprising two or more O-rings around a periphery thereof;
an inlet channel connecting the source of compressed gas to the hollow chamber in the housing;
an outlet channel connecting the hollow chamber to the mixing chamber;
wherein the O-rings are positioned on the stem relative to the inlet channel and the outlet channel such that in a first position of the actuation assembly, one O-ring seals the inlet channel at the hollow chamber and, as the actuation assembly is actuated, the stem moves such that the outlet channel at the hollow chamber is or continues to be sealed by another O-ring, and the inlet channel is unsealed from the one O-ring, allowing into the hollow chamber an amount of gas, while at that point or thereafter a pump is activated to move the liquid into the mixing chamber; wherein when the actuation assembly is thereafter released, moving back to its first position, the stem moves such that the inlet channel is first sealed by the one O-ring and the outlet channel is unsealed from the another O-ring, allowing the gas in the hollow chamber to rapidly move into the mixing chamber to mix with the liquid therein, to produce a stream of fluid droplets which are directed to and out the nozzle assembly of the appliance.

2. The appliance of claim 1, wherein the inlet and outlet channels are on opposite sides of the hollow chamber.

3. The appliance of claim 1, wherein the outlet channel is unsealed from the another O-ring by action of the gas in the hollow chamber.

4. The appliance of claim 1, wherein the pump is actuated by a distal end of the stem of the actuation assembly.

5. The appliance of claim 1, wherein actuation of the actuation assembly results in actuation of an additional function.

6. The appliance of claim 5, wherein the additional function is a status display of operation of the appliance.

7. The appliance of claim 1, wherein the switch housing is arranged transversely to a longitudinal direction of the oral care appliance, such that the stem moves back and forth within the hollow chamber in the switch housing transversely to the longitudinal direction of the appliance.

8. The appliance of claim 1, wherein the inlet channel to the hollow chamber is at a different longitudinal position along the hollow chamber than the outlet channel to the mixing chamber.

9. The appliance of claim 1, wherein the actuation assembly includes a button member for contact with a finger of a user and a spring member biasing the actuation assembly in its first position.

10. An oral care appliance comprising:
a source of compressed gas, a source of fluid, a mixing chamber for mixing the gas and the fluid to produce a stream of fluid droplets which are directed out through a nozzle assembly;
a switch housing having a hollow chamber therein, the switch housing including an inlet to the hollow chamber and an outlet from the hollow chamber; and
an actuator assembly having a stem portion which extends into the switch housing, including elements mounted thereon which maintain the hollow chamber outlet closed when opening the hollow chamber inlet, actuating a pump which directs fluid into the mixing chamber, and then opening the outlet while having previously closed the inlet, allowing gas present in the hollow chamber to move into the mixing chamber.

11. The appliance of claim 10, wherein the outlet is opened by action of the gas in the hollow chamber.

12. The appliance of claim 10, when said elements are O-rings.

13. The appliance of claim 10, wherein the inlet includes a first channel extending between the source of compressed gas and the hollow chamber and the outlet includes a second channel between the hollow chamber and the mixing chamber, wherein the first and second channels are on opposing sides of the hollow chamber and have different longitudinal positions along a length of the hollow chamber.

14. An oral care appliance, comprising:
   an appliance housing;
   a source of compressed gas;
   a source of liquid;
   a mixing chamber within the housing for mixing gas from the source thereof and liquid from the source thereof;
   a nozzle member through which a stream of fluid droplets is directed from the mixing chamber; and
   a multi-function switch including a switch housing having a hollow chamber therein; an actuator assembly having sealing elements mounted at a periphery of a stem portion thereof which is positioned in the hollow chamber; and an inlet channel connecting the source of gas with the hollow chamber and an outlet channel connecting the hollow chamber with the mixing chamber, wherein the sealing elements are mounted on the stem portion relative to the inlet and outlet channels such that the outlet channel is sealed when the inlet channel opens, allowing gas into the hollow chamber, and such that the inlet channel is sealed when the hollow chamber is full of gas and the outlet channel is open, allowing the gas in the hollow chamber to move into the mixing chamber, where it mixes with the liquid therein to produce a stream of fluid droplets, which move out through the nozzle member.

* * * * *